United States Patent [19]

Bellotti et al.

[11] 4,436,620
[45] Mar. 13, 1984

[54] INTEGRAL HYDRAULIC CIRCUIT FOR HEMODIALYSIS APPARATUS

[75] Inventors: Marc Bellotti, Winnetka; Richard P. Goldhaber, Libertyville; Earl G. Phillips, Barrington; Theodore H. Toch, Streamwood, all of Ill.

[73] Assignee: Baxter Travenol Laboratories, Inc., Deerfield, Ill.

[21] Appl. No.: 57,387

[22] Filed: Jul. 13, 1979

Related U.S. Application Data

[63] Continuation of Ser. No. 794,755, May 19, 1977, abandoned.

[51] Int. Cl.³ ............................................. B01D 31/00
[52] U.S. Cl. .................................... 210/90; 210/321.3
[58] Field of Search ............................... 138/118, 115; 128/350 R, DIG. 24; 174/47; 210/90, 85, 96 M, DIG. 23, 94, 22, 321 B, 96.2, 927, 321.3

[56] References Cited

U.S. PATENT DOCUMENTS

| 3,527,572 | 9/1970 | Urkiewicz | 210/DIG. 23 |
| 3,774,762 | 11/1973 | Lichtenstein | 210/94 |
| 3,778,973 | 12/1973 | Martinez | 210/23 X |
| 3,906,935 | 9/1975 | Raia et al. | 128/DIG. 24 |
| 3,908,653 | 9/1975 | Kettering | 210/90 X |
| 3,964,479 | 6/1976 | Boag et al. | 210/90 X |
| 4,077,882 | 3/1978 | Gangemi | 210/90 |

*Primary Examiner*—Frank A. Spear, Jr.
*Attorney, Agent, or Firm*—Paul C. Flattery; Garrettson Ellis

[57] ABSTRACT

A one-piece hydraulic circuit is provided for use with a blood dialyzer for for performing functions currently performed with a multiplicity of blood inlet and outlet sets and related items comprising flexible tubing and the like.

16 Claims, 5 Drawing Figures

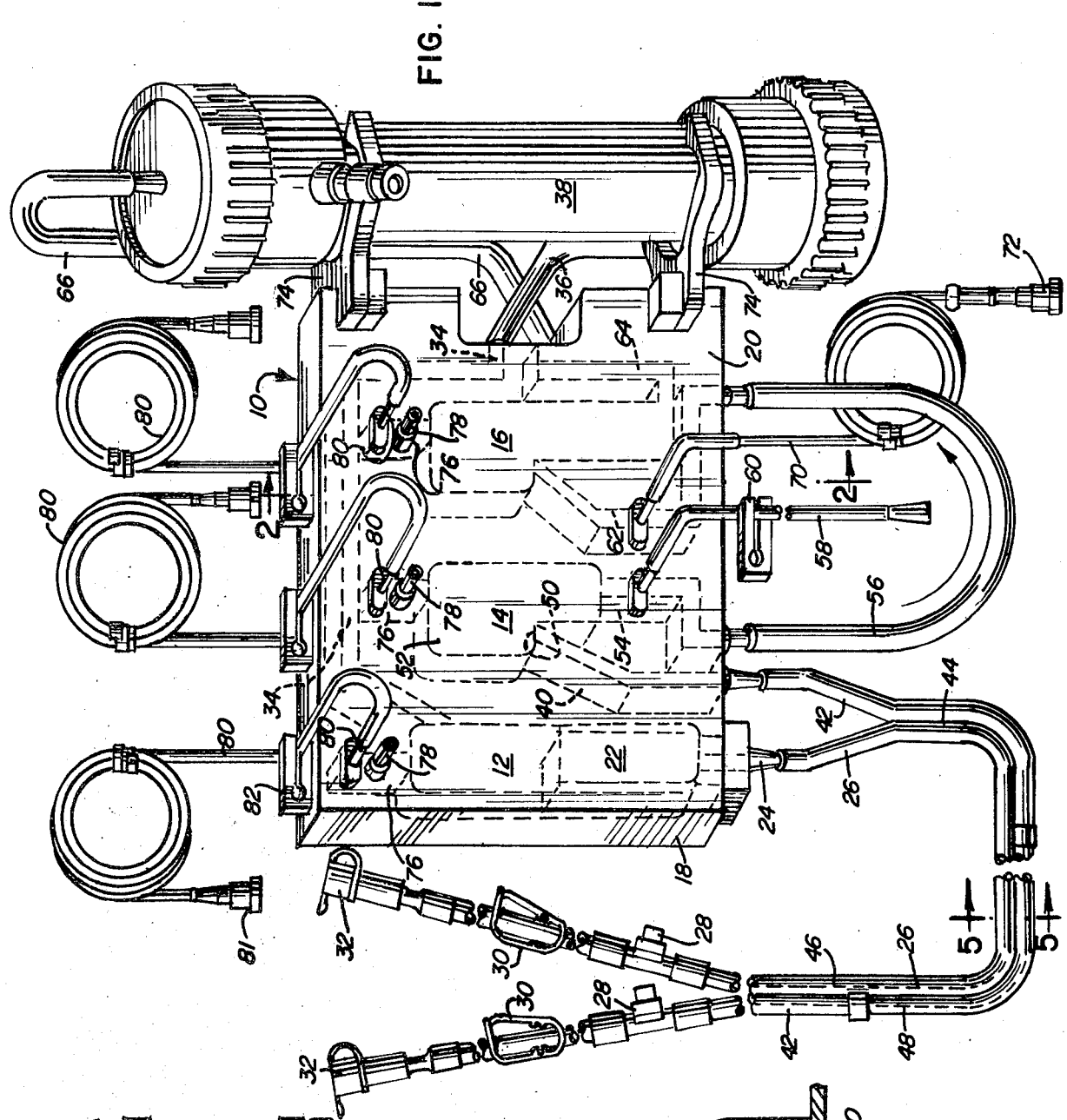

INTEGRAL HYDRAULIC CIRCUIT FOR HEMODIALYSIS APPARATUS

CROSS-REFERENCE TO RELATED APPLICATION

This application is a continuation of U.S. application Ser. No. 794,755, filed May 19, 1977, now abandoned.

BACKGROUND OF THE INVENTION

Hemodialysis apparatus for artificial kidneys generally comprises a supported, semi-permeable membrane made of a cellophane-type material, positioned in a casing to provide a blood flow path along one side of the membrane and a dialysis solution flow path along the other side, for diffusion exchange across the membrane between the blood and the dialysis solution without the direct intermixing of the two liquids.

In the actual hemodialysis process, a considerable number of processing steps are required during the operation for bringing the blood to the hemodialzer, and withdrawing it from the hemodialyzer for return to the patient. In the presently-conventional arterial and venous sets which are used to withdraw blood from a patient, convey it to the dialyzer, and return it again to the patient, bubble traps, filters, sterile access sites for injection needles, and access sites for pressure monitor equipment may all be included on the sets, which primarily comprise flexible, blood compatible plastic tubing. Accordingly, in the present technology of dialysis, two different and separate long, tubular sets are utilized, the arterial set upstream from the dialyzer in terms of blood flow, and the venous set downstream from the dialyzer.

Hence, to set up a dialysis procedure, a dialyzer must be selected, and the nurse must also separately obtain an arterial set and a venous set. The packaging of all of these devices must be opened, and the devices repsectively must be connected and assembled together, with other auxiliary equipment being also added to the system. This requires the services of a highly trained technician, who must make a considerable number of connections between the sets and the dialyzer, flawlessly and without error.

In accordance with this invention, a one-piece hydraulic circuit is provided to replace many of the functions of the arterial inlet and outlet sets, and auxiliary equipment. The one-piece hydraulic circuit may be connected to the dialyzer itself at the time of manufacture, if desired. The set-up of the dialysis system prior to use is thus greatly simplified, eliminating many of the connections which must be made by the technician at the site of use, which, in turn, reduces the possibility of error, and contamination of the system during the assembly and connection process. Furthermore, the system of this invention is compact and simplified, saving a considerable amount of valuable space around the bed during the dialysis procedure.

DESCRIPTION OF THE INVENTION

In accordance with this invention, a one-piece hydraulic circuit for use with a blood dialyzer comprises a rigid, unitary member defining spaced first, second and third chambers therein. A first port communicates with the first chamber, and is adapted for connection with a venous line of a patient. A second port also communicates with the first chamber, and is adapted for connection with the outlet of a blood dialyzer.

The second chamber communicates with a third port which in turn is adapted for connection with an arterial line of the patient. The second chamber also communicates with a fourth port adapted for connection with an end of blood pump tubing.

The third chamber communicates with a fifth port which is adapted for connection with the other end of the blood pump tubing. The third chamber also communicates with a sixth port adapted for connection with the inlet of the blood dialyzer.

In the specific embodiment shown, the flow of blood enters the second chamber from the artery of the patient, in which point any bubbles are collected at the top of the chamber, for example, bubbles injected through an injection site into the line to monitor the flow velocity. The fourth outlet port is generally positioned at the bottom end of the chamber to facilitate the bubble trapping characteristic. Blood flows out of the fourth port through pump tubing, which may be installed in a conventional roller pump device to power the flow of blood through the apparatus.

Passing through the pump tubing, the blood enters the fifth port and the third chamber, where an additional bubble trapping function takes place, to prevent bubbles from entering the dialyzer. The sixth port exits from the bottom of the third chamber, and is connected with tubing which, in turn, leads to the blood inlet of the dialyzer.

Passing through the dialyzer, the blood exits from the outlet which, in turn, is in connection with the second port of the first chamber. The blood enters the first chamber, then generally passing through the air-blocking filter to prevent infusion of air into the patient. The blood then passes through the first port of the first chamber, which is in communication with tubing connected to the venous system of the patient.

Accordingly, the highly-desirable bubble-trapping function, plus a blood filtering function, may be provided by the one-piece hydraulic circuit of this invention.

Additionally, injection-type access sites, for example, for removal of air, are provided, as well as a site for measuring chamber pressure. Also, a saline infusion and a heparin line may be added to the device where desired.

In the drawings,

FIG. 1 is a perspective view of the one-piece hydraulic circuit member of this invention, connected to a hollow fiber-type dialyzer, and further connected to auxiliary tubing of various types.

FIG. 2 is a transverse sectional view of the one-piece hydraulic circuit member of this invention, taken along line 2—2 of FIG. 1.

FIG. 3 is a similar transverse sectional view of another embodiment of the hydraulic circuit member of this invention.

FIG. 4 is a detailed sectional view of an alternative sensing member as a replacement for member 80.

FIG. 5 is a sectional view taken along line 5—5 of FIG. 1.

Referring to the drawings, hydraulic circuit member 10 is shown to be made of a rigid piece of flat plastic, defining chambers 12, 14 and 16 within the plastic piece.

As shown in FIG. 2, plastic piece 10 may comprise a lower flat plastic plate 18 which defines the chambers and ports utilized herein as cutout portions. Plastic plate 18 may be sealed by a cover member 20 to enclose said cutout portions.

Alternatively, as in FIG. 3, both plastic plate 18a and cover 20a may be equally-sized pieces, both defining cutout portions for chambers 12, 14, and 16, and for the various ports.

Chamber 12 may preferably include a blood filter member 22, surrounding a first port or conduit 24, which, in turn, provides communication between chamber 12 and flexible tubing 26, adapted for communication with the vein of a patient. In any conventional manner, venous tubing 26 may contain a sterile injection site 28 for blood sampling or medication, clamp 30, and removable sterile cover 32 for sealing the tubing. Tubing 26 may be connected to a fistula needle for access to the patient, or an arterio-venous shunt, or any other desired means for communication with the patient's venous system.

Chamber 12 also defines a second port or conduit 34 which is shown to define an elongated channel for communication with a blood outlet conduit 36, receiving blood from the blood of dialyzer 38. Dialyzer 38 is shown to be commercially available hollow fiber dialyzer in this particular embodiment, although this invention may be used with any type of dialyzer.

Accordingly, blood outflow from the dialyzer 38 enters chamber 12 at an upper end, and passes through filter 22 into venous line 26 for reinfusion to the patient.

Second chamber 14 is in communication through port or conduit 40 with blood tubing 42, which may be in communication with the arterial system of a patient. Tubing 42 also may carry a conventional injection site 28, clamp 30, and sterile cover 32, as well as any other conventional equipment. Also, if desired, tubings 26 and 42 may be integrally connected together by a fine web 44 of plastic material, which may be torn apart as far along the length of the respective tubings 26, 42 as desired, but otherwise which holds the two tubings together in an integral manner, to avoid the confusing and inconvenient separate wandering and coiling of the respective tubes.

Tubes 26 and 42 may be conveniently co-extruded as a single piece to define the frangible web 44 between them. Appropriate indicia such as colored lines 46, 48 may be placed on the respective tubing 26, 42 for identification of the tubing.

Blood from tubing 42 passes through third port 40, preferably at an entry port 50 which is intermediate along the length of chamber 14, to provide an upper area 52 in the chamber for receiving and retaining gas bubbles.

The blood then is withdrawn from chamber 14 downwardly from the lower end through a fourth port or conduit 54 which, in turn, is in communication with a length of blood pump tubing 56. Tubing 56 may be emplaced within a roller-type blood pump for movement of the blood from chamber 14 to chamber 16, and to power the blood flow through the entire system.

If desired, saline solution infusion line 58, controlled by clamp 60, may communicate in sterile manner with port 54 for use as desired.

The blood from tubing 56 enters fifth port or conduit 62, which leads to chamber 16, communicating with the chamber at a mid-point thereof in a manner similar to entry point 50, and for the similar purpose of providing a bubble-trapping capability to the chamber.

Blood is withdrawn from chamber 16, impelled by the action of a blood pump on tubing 56, through the sixth port or conduit 64, which, in turn, communicates with an inlet line 66 leading into the blood inlet of the dialyzer 38.

A heparin administration line 70 may be provided in communication with port 62 if desired, carrying a sterile end seal 72 for connection with any desired heparin administration device for administering measured quantities of heparin over a period of time to the blood circuit.

Accordingly, blood enters from the patient's arterial system through tubing 42, passing through port 40 to chamber 14 for bubble removal, and from there to pump tubing 56 through port 54.

Impelled by the blood pump, the blood is forced onwardly through port 62 into chamber 16 for additional bubble removal, and from there through port 64 into the dialyzer 38. Dialyzed blood passes along port 34 into chamber 12. Then, the blood passes through filter 22, through port 24, and into venous tubing 26 for return to the patient.

Gripper members 74 are carried by hydraulic circuit member 10 for grasping, as shown, the dialyzer 38, to provide a convenient, one-piece structure including both the dialyzer and much of its circuitry. The entire structure may have a hanger or attachment member (not shown) for hanging or clamping on an IV pole or the like as desired.

Each of the chambers 12, 14, 16 defines an upper projecting channel 76. Connected to this channel in each case is a sealed injection site member 78, which may include a latex member compression fitted into a tubular member in a manner similar to the injection site members which are in present commercial use on the arterial and venous sets for dialysis sold by the Artificial Organs division of Travenol Laboratories, Inc., Deerfield, Ill. Excess air trapped in the chambers may be removed by a needle and syringe through site 78.

Tubing 80 is also in communication with upper projecting channel 76 in each case. Sealed end 81 may be opened and connected to a manometer or other pressure measuring device to obtain a direct measurement of the pressure within chambers 12, 14 or 16. Clamp 82 is also provided to seal tubing 80 when not in use. As an alternative structure to replace tube 80 with its direct connection to each of the chambers 12, 14 or 16, a pressure-sensing member 84 may be provided which measures the pressure of the respective chambers in a non-invasive manner.

As shown in FIG. 4, pressure-sensing member 84 comprises a housing 86 which fits over an aperture 88 in part of the wall of hydraulic circuit member 10 which is in communication with channel 76. A liquid-impermeable, flexible diaphragm 90 is positioned across aperture 88, positioned in the effective sensing range of a transducer 92, which is adapted to sense the degree of outward or inward bulging of diaphragm 90, in response to positive or negative pressure in the channel 76.

Accordingly, the pressure within each of chambers 12, 14, 16 is reflected by the degree of outward or inward bulging of diaphragm 90. This, in turn, is sensed by transducer 92 and communicated along electrical line 94 to a conventional readout device so that, as desired, the pressure in the respective chambers 12, 14 and 16 can be monitored, while the system remains sealed.

If desired, dialyzer 38 may be made integrally with hydraulic circuit member 10, in which the fibers and potting compound conventionally used in fiber dialyzers, or other membrane material and supports, are placed in an aperture defined in circuit member 10, to provide the dialysis function as an integral port of circuit member 10.

The above has been offered for illustrative purposes only, and is not for the purpose of limiting the invention of this application, which is as defined in the claims below.

That which is claimed is:

1. In a hydraulic circuit member for use with a membrane diffusion device, which comprises a unitary member defining a plurality of blood-receiving chambers, and conduit means communicating between said blood-receiving chambers, for directing, receiving, and processing blood passing through said membrane diffusion device, in which at least one of said blood receiving chambers defines a transversely-enlarged upper chamber portion connected by a step wall which abruptly narrows the bottom end of said enlarged chamber area to a lower chamber portion of lesser transverse dimension, and points of communication of said conduit means with said chamber, including an inlet spaced from the bottom of said chamber and communicating directly with said enlarged upper chamber portion in an upwardly-pointing direction through said step wall, and an outlet positioned adjacent the end of said lower portion remote from said enlarged, upper portion of said chamber, said chamber defining vent means for gases at its upper end and constituting an improved bubble trap for blood when blood is introduced through said inlet and withdrawn through said outlet.

2. The hydraulic circuit member of claim 1 in which said circuit member comprises a rigid, unitary member made of a flat plastic plate having chambers and ports defined by cut-out portions in said flat, plastic plate, and said plastic plate is sealed by a cover member to enclose said cut-out portions.

3. A one-piece hydraulic circuit member for use with a blood dialyzer for directing and controlling blood flow which comprises, a rigid, unitary member defining spaced chambers for receiving blood, and conduit means communicating with said chambers adapted respectively for connection with a venous line of a patient, the blood inlet and outlet of a blood dialyzer, an arterial line for the patient, and ports for communication with blood pump tubing, in which at least some of the chambers defined within said rigid unitary member consitute blood-receiving chambers defining a distinct, enlarged chamber area at an upper portion thereof connected by a step wall to a lower portion thereof which is not transversely enlarged, and points of communication of said conduit means with said chamber including a first point of communication spaced from the bottom of said chamber and communicating directly with said distinct enlarged chamber area in an upwardly pointing direction through said step wall, and a second point of communication of said conduit means with said chamber being positioned adjacent the end of said lower portion remote from the upper portion of said chamber, and venting means provided at the top of said chamber, whereby improved bubble-trapping capabilities are provided to blood in said chamber which is introduced to the chamber through said first point of communication and withdrawn through said second point of communication.

4. In a hydraulic circuit member for use with a membrane diffusion device, which comprises a unitary, rigid, flat plastic member defining a plurality of blood-receiving chambers, conduit means for communicating between said blood-receiving chambers, said membrane diffusion device, and the arterial and venous lines of a patient, in which at least one of said blood receiving chambers define an aperture, said aperture being sealed by a liquid-impermeable, flexible diaphragm, and pressure sensing means adjacent said diaphragm outside of said chamber, whereby displacement of said diaphragm in response to pressure in said chamber is sensed by said pressure sensing means, said chamber defining a distinct, enlarged chamber area at an upper portion thereof with respect to the lower portion, said enlarged chamber area being separated from the lower portion by a step wall abruptly narrowing the lower end of said enlarged chamber area, and communication apertures of said conduit means with said chamber including a first aperture spaced from the bottom of said chamber and communicating directly with said enlarged chamber area in an upwardly-pointing direction through said step wall, and a second aperture of said conduit means being positioned adjacent the end of said lower portion, remote from the upper portion of said chamber, said chamber defining as vent means adjacent its upper end, whereby blood entering said chamber through said first aperture is subjected to improved bubble-trapping action, and blood may be withdrawn from said second aperture.

5. A hydraulic circuit member for use with a blood dialyzer in which first, second and third chambers are present in said unitary, rigid member, at least one of which is of the shape as defined by claim 4 and further including a first port, communicating with said first chamber and adapted for connection with a venous line of a patient, and a second port communicating with said first chamber and adapted for connection with the outlet of a blood dialyzer; a second chamber communicating with a third port, said third port being adapted for connection with an arterial line of a patient, said second chamber also communicating with a fourth port adapted for connection with blood pump tubing, and a third chamber communicating with a fifth port adapted for connection with said blood pump tubing, said third chamber also communicating with a sixth port adapted for connection with the inlet of said blood dialyzer.

6. The hydraulic circuit member of claim 5 in which said first chamber contains a blood filter positioned for filtering gases from the blood flow through said first port.

7. The one-piece hydraulic circuit member of claim 5 in which said chambers and ports are defined by cutout portions in a flat plastic plate, said plastic plate being sealed by a cover member to enclose said cut-out portions.

8. The one-piece hydraulic circuit member of claim 5 in which a saline infusion line is in communication with said port.

9. The hydraulic circuit member of claim 5 in which a heparin line is in communication with said fifth port.

10. The hydraulic circuit member of claim 5 in which a sealable injection site provides communication by means of an injection needle to said chambers.

11. The hydraulic circuit member of claim 5 which defines means for carrying a dialyzer for blood.

12. The hydraulic circuit member of claim 11 in which said first port is connected to a venous line and said third port is connected to an arterial line, said arterial and venous lines being joined together along one side along a major portion of their lengths.

13. The hydraulic circuit member of claim 12 in which said third and fifth ports respectively communicate with said first apertures in said second and third chambers while said fourth and sixth ports communicate respectively with said second and third chambers at said second apertures.

14. The hydraulic circuit member of claim 13 in which said first port communicates with the lower end of said first chamber and said second port communicates adjacent the upper end of said first chamber.

15. In a hydraulic circuit member integral with a membrane diffusion device for blood, said hydraulic circuit member defining a rigid, unitary housing member defining a plurality of blood-receiving chambers, and conduit means communicating in a blood flow path between said blood-receiving chambers and the membrane diffusion device, for receiving and processing blood passing through said membrane diffusion device, and blood-receiving chambers being defined by the walls of said rigid housing, and defining means for collecting and removing bubbles from the circulating blood, said rigid housing being capable of operating under negative pressure conditions without collapse of the conduit means and blood-receiving chambers, said rigid housing comprising:

a rigid, unitary member made of a flat, plastic piece, at least part of said blood-receiving chambers and conduit means being defined by cut-out portions to said flat, plastic piece, said flat, plastic piece being sealed by a cover member to enclose said cut-out portions.

16. In a hydraulic circuit member integral with a membrane diffusion device for blood, said hydraulic circuit member defining a rigid, unitary housing member defining a plurality of blood-receiving chambers, and conduit means communicating in a blood flow path between said blood-receiving chambers and the membrane diffusion device, for receiving and processing blood passing through said membrane diffusion device, said blood-receiving chambers being defined by the walls of said rigid housing, and defining means for collecting and removing bubbles from the circulating blood, said rigid housing being capable of operating under negative pressure conditions without collapsing of the conduit means and blood-receiving chambers, said rigid, unitary housing member defining at least one blood-receiving chamber which, in turn, defines a distinct enlarged chamber area at an upper portion thereof connected by a step wall to a lower portion thereof which is not transversely enlarged, and a blood inlet spaced from the bottom of said chamber and communicating directly with said enlarged upper chamber portion in an upwardly-pointing direction through said step wall, and an outlet positioned adjacent the end of said lower portion remote from said enlarged upper portion of said chamber, and vent means for gases being positioned at its upper end.

* * * * *